United States Patent
Zhang et al.

(10) Patent No.: US 10,408,803 B2
(45) Date of Patent: Sep. 10, 2019

(54) MASS SPECTROMETER DETECTION AND ANALYSIS METHOD

(71) Applicant: Huajun Zhang, Zhangjiagang (CN)

(72) Inventors: Huajun Zhang, Zhangjiagang (CN); Ning Ying, Zhangjiagang (CN)

(73) Assignee: Huajun Zhang, Zhangjiagang (CN)

( * ) Notice: Subject to any disclaimer, the term of this patent is extended or adjusted under 35 U.S.C. 154(b) by 18 days.

(21) Appl. No.: 15/548,864

(22) PCT Filed: Sep. 6, 2016

(86) PCT No.: PCT/CN2016/098204
§ 371 (c)(1),
(2) Date: Aug. 4, 2017

(87) PCT Pub. No.: WO2017/041696
PCT Pub. Date: Mar. 16, 2017

(65) Prior Publication Data
US 2018/0024099 A1    Jan. 25, 2018

(30) Foreign Application Priority Data

Sep. 9, 2015 (CN) .......................... 2015 1 0570497

(51) Int. Cl.
*G01N 30/72* (2006.01)
*H01J 49/00* (2006.01)
(Continued)

(52) U.S. Cl.
CPC .......... *G01N 30/72* (2013.01); *H01J 49/0031* (2013.01); *G01N 30/7206* (2013.01);
(Continued)

(58) Field of Classification Search
CPC ............... G01N 2560/00; G01N 30/72; G01N 30/7206; G01N 30/7233; H01J 49/0031;
(Continued)

(56) References Cited

U.S. PATENT DOCUMENTS

| | | | | |
|---|---|---|---|---|
| 5,481,476 A | * | 1/1996 | Windig | ...................... G01J 3/28 702/31 |
| 7,804,062 B2 | * | 9/2010 | Meija | .................. H01J 49/0036 250/282 |

FOREIGN PATENT DOCUMENTS

WO    2007112597 A1    10/2007

OTHER PUBLICATIONS

Xia, Zhenzhen, et al. "Band target entropy minimization for retrieving the information of individual components from overlapping chromatographic data." Journal of Chromatography A 1411 (2015): 110-115.*

(Continued)

*Primary Examiner* — Wyatt A Stoffa
(74) *Attorney, Agent, or Firm* — Wang Law Firm, Inc.

(57) ABSTRACT

The present invention provides a mass spectrometric detection and analysis method, comprising the steps of: selecting, as a perturbation condition, one or more parameters of a mass spectrometer during detection, setting a set of different numeric values for the perturbation condition, detecting by the mass spectrometer a substance to be detected under the different numeric values of the perturbation condition to obtain a set of mass spectrometric data; calculating the set of obtained mass spectrometric data by an entropy minimization algorithm to obtain independent ions in the mass spectrometric data and kinetic processes thereof; and performing mass spectrometric analysis on the basis of the obtained independent ions and kinetic processes thereof. The method of the present invention can quickly and accurately perform qualitative analysis on the substances to be detected, especially on substances that are difficult to distinguish with existing mass spectrometric techniques such as isomers and homologs. The method of the present invention can also perform analysis by the difference between the kinetic processes and thereby determine the nature of such (Continued)

substances. The method of the present invention has a very broad application prospect due to its simple operation and accurate results of analysis.

20 Claims, 9 Drawing Sheets

(51) Int. Cl.
    *H01J 49/14* (2006.01)
    *H01J 49/16* (2006.01)
(52) U.S. Cl.
    CPC ...... *G01N 2560/00* (2013.01); *H01J 49/0036* (2013.01); *H01J 49/145* (2013.01); *H01J 49/165* (2013.01)
(58) Field of Classification Search
    CPC .... H01J 49/0036; H01J 49/145; H01J 49/147; H01J 49/165
    See application file for complete search history.

(56) References Cited

OTHER PUBLICATIONS https://en.wikipedia.org/wiki/Mass_spectrometry, retrieved from Aug. 19, 2015 by web.archive.org on Dec. 6, 2018, (Year: 2015).*
Lin Guang-Chuan et al.; "Analysis of Unknown Components in Rose Essential Oil by Entropy Minimization Algorithm"; Journal of Chinese Mass Spectrometry Society, Sep. 2015, vol. 36, No. 5, pp. 448-453.

* cited by examiner

MASS SPECTROMETER DETECTION AND ANALYSIS METHOD

TECHNICAL FIELD OF THE INVENTION

The present invention relates to the field of chemical analysis and in particular to a mass spectrometric detection and analysis method.

BACKGROUND OF THE INVENTION

Mass Spectrometers (MS), as widely applied chemical analysis instruments, have been applied in various fields. In a certain mass spectrometer, in the ion source portion, a substance gets or loses charges (ionization) by various means and becomes charged ions. Then, charged ions with a different mass-to-charge ratio are filtered in accordance with different principles and then reach a detector. In this way, a mass spectrum is obtained. In the mass spectrometry, there are many ionization techniques: Electron Ionization (EI) and Chemical Ionization (CI) for the gas chromatography-mass spectrometry, and Electrospray Ionization (ESI) and Atmosphere Pressure Chemical Ionization (APCI) and the like for the liquid chromatography-mass spectrometry.

The analysis of the mass spectrum, especially the analysis of the mass spectrum of unknown substances, is very important. The existing various mass spectrometric data is to be analyzed by various experiences. For example, in EI-MS which is mainly used for detecting volatile substances, molecular ion peaks may be found by several rules (for example, Nitrogen Rule), and then the mass spectrometric peaks of various fragments are deduced according to the isotope and energy rules, and finally the structures of the substances represented by the mass spectrums are obtained. There are many unknown components in natural products and traditional Chinese medicines. On the other hand, in EI-MS, for known substances, the mass spectrums and the mass spectrometric database (for example, NIST database) are mainly used for comparison to obtain the structural information about the components in the existing techniques. However, for traditional Chinese medicines with complicated components, since there are many isomeric components therein, most fragments in their mass spectrums have the same position, only different in abundance in some places. In this case, it is even difficult to determine a certain isomer by comparing the mass spectrum of a pure substance with the NIST database.

In the liquid chromatography-mass spectrometry (ESI-MS, APCI-MS, etc.) and solid chromatography-mass spectrometry, usually, during the electrification, the substances will not break, and instead, will form complexes together with some ions ($Na^+$, $K^+$, $H^+$) or even form polymers and have several charges. Therefore, in the liquid chromatography-mass spectrometry, it is very difficult to determine which compound the substance is by the mass spectrometric peak in the first-stage mass spectrometry ($MS^1$). Instead, it is able to determine the information about a compound represented by one mass spectrometric peak only, by multi-stage fragmentation using multi-stage mass spectrometry ($MS^n$).

In the existing mass spectrum analysis, the analysis of the mass spectrum is a very professional subject. Although there have been many rules for analysis, only few people are proficient in this because of high requirements on the desired subject knowledge and coverage of a wide range of knowledge. The existing analysis of the mass spectrum is costly due to these reasons. Thus, the application of the analysis of the mass spectrum is restricted.

In the mass spectrometry, the ionization and fragmentation of molecules in the ion source of the mass spectrometer is a very complicated process in which various different ions are generated. The process of ion fragmentation in the mass spectrometry is a complicated reaction process. The ion fragmentation rule in the mass spectrometry is influenced by the mass spectrometry itself and the environment. The generated molecular ions and fragment ions are influenced by their own structure and the internal energy, and also influenced by the charge generation process and the environment. For example, the kinetic process of ion fragmentation can be influenced by all the EI voltage, degree of vacuum and ion accelerating voltage. In the mass spectrometry, the ion generation process is very short, roughly only about 10 milliseconds. Therefore, experimentally, it is very difficult to capture the ion fragmentation process. The common method is to analyze by the method of quantum mechanics. There has been no report on the studies on the kinetic process of ion fragmentation in the mass spectrometry by other methods.

Various mathematical methods have been widely used in analytical instruments and various analysis methods, to aid in solving various problems in the analysis, for example, the problem of baselines. Those mathematical methods are collectively called stoichiometry. It is a subject worthy of study to analyze the fragmentation processes (kinetic processes) of those ions in the mass spectrometry by stoichiometry.

It is significant meaningful to smoothly understand the fragmentation process of ions in the mass spectrometry, which can help the researchers to find new compounds more quickly and easily, better understand the structural information of various types of compounds, distinguish between similar compound structures (for example, isomers) by the obtained kinetic information, and better determine the nature of substances.

Independent Components

Independent components refer to certain components, functional groups or fragments in the mixtures, the behavior pattern of which is free of the interference of other components, functional groups or fragments. The behavior pattern of those independent components remains consistent and varying. Although the detected amplitude (for example, abundance) changes because of the change in their concentration, their features (for example, pure spectrum) remain unchanged. For example, in the mass spectrum of a mixture, the independent components may be pure components in the mixture, and the pure spectrum of the independent components remains consistent at different sampling times without being influenced by other components. During the ion fragmentation of a pure substance in the mass spectrometry, the independent components may be certain individual charged functional groups or fragments. Since the independent components have constant mass and composition, their mass spectra (including isotopic peaks) are also constant. When explained mathematically, the comprehensive presentation of a complex containing many independent components is the linear summation of the independent components, i.e., the linear system. The actual linear system will be somewhat different from the linear system because of the involved processes such as electronic sampling and data processing, and various noises.

Entropy Minimization Algorithms

Stoichiometry and chemical dynamics belong to two subjects. Amongst other things, stoichiometric methods, i.e., the entropy minimization algorithms, are used for the discovery of intermediate products of chemical reactions and the analysis of mixed spectra. Entropy minimization algorithms (EMs) were developed on the basis of Shannon Entropy. Shannon Entropy was originally published in 1948 [C. E. Shannon, The Bell System Technical Journal, 27 (1948) 379-423]. It is an academic term in the field of information, for measuring the uncertainty of random parameters.

Marc Garland is the first one who found the application of Shannon Entropy in chemical analysis [Y. Z. Zeng, M. Garland, Analytica Chimica Acta, 359 (1998) 303-310]. He published BTEM (Band-Target Entropy Minimization) in 2002 [W. Chew, E. Widjaja, M. Garland, Organometallics, 21 (2002) 1982-1990]. In this method, the infrared spectrum of reactants and resultants in a certain closed reaction system is reconstructed by using the entropy minimization algorithm by studying the closed reaction system and performing infrared data sampling at different reaction time.

Although the kinetic process of the reaction can be studied by the entropy minimization algorithms, those methods are mainly used for reconstructing the pure spectra of components from the mixed spectra. In 2003, H. J. Zhang et al. published the tBTEM (Weighted Two-Band Target Entropy Minimization) [H. J. Zhang, M. Garland, Y. Z. Zeng, P. Wu, J Am Soc Mass Spectrom, 14 (2003) 1295-1305]. This method is mainly used for the analysis of mass spectra. In 2006, H. J. Zhang et al. published the MREM (Multi-Reconstruction Entropy Minimization) [H. J. Zhang, W. Chew, M. Garland, Applied Spectroscopy, 61 (2007) 1366-1372]. In this method, the global optimization is replaced with the local optimization, and no search range is to be specified manually. The function of automatically searching for pure spectra is truly realized.

In 2009, the entropy minimization algorithms were eventually applied to the analysis of ultraviolet spectra [F. Gao, H. J. Zhang, L. F. Guo, M. Garland, Chemometrics and Intelligent Laboratory Systems, 95 (2009) 94-100].

SUMMARY OF THE INVENTION

In order to overcome defects in the existing field of mass spectrometric detection and analysis, an objective of the present invention is to provide a novel mass spectrometric detection and analysis method.

For this purpose, the mass spectrometric detection and analysis method of the present invention includes the steps of:

1) selecting, as a perturbation condition, one or more parameters of a mass spectrometer during detection, setting a set of different numeric values for the perturbation condition, detecting by the mass spectrometer a substance to be detected under the different numeric values of the perturbation condition to obtain a set of mass spectrometric data;

2) calculating the set of mass spectrometric data obtained in the step 1) by an entropy minimization algorithm to obtain independent ions in the mass spectrum and the kinetic processes thereof; and 3) performing mass spectrometric analysis on the basis of the independent ions and the kinetic processes thereof obtained in the step 2).

Wherein, the perturbation condition includes, but not limited to, electric field strength, magnetic field strength, radiation strength, degree of vacuum, size and type of collided molecules, and wavelength or strength of an excitation light source.

Wherein, before the step 2), the method further includes: pre-processing the set of mass spectrometric data obtained in the step 1). The pre-processing is to perform linear transformation on a single piece of mass spectrometric data in the set of mass spectrometric data (for example, unitization, etc.). The pre-processing may also be noise and background processing.

In the present invention, the mass spectrometer includes, but not limited to, a gas chromatography-mass spectrometer or a liquid chromatography-mass spectrometer.

The ionization mode for the mass spectrometer includes, but not limited to, chemical ionization, electron ionization, electrospray ionization or atmospheric pressure chemical ionization.

In the existing mass spectrometric analysis, usually in a certain ionizaiton mode (for example, EI, CI, APCI, ESI), the detection of a substance to be detected is performed at fixed parameters to obtain a mass spectrum (referred to as "one-dimensional mass spectrum" herein). However, using same ionization method and different parameter setting, the ionization and fragmentation processes of substances are different due to their different chemical bond energy and spatial structures. For example, although the benzene ring structure is more difficult to break than the long-chain alkane, under a same parameter setting, it is still unable to distinguish between the benzene ring and the long-chain alkane in the one-dimensional mass spectrum. However, if analysis is performed under a series of different parameter settings, it is convenient to judge whether it is the benzene ring or the long-chain alkane since the benzene ring and the long-chain alkane break under different perturbation conditions. Studying the fragmentation process of a same substance under different perturbation conditions is called the mass spectrum fragmentation kinetic study in the present invention.

In the EI-MS analysis, the molecules are easily fragmented when the EV is too high (for example, 100V), and it is basically unable to detect any molecular ion peak. Meanwhile, since the EV is too high, the fragments are concentrated in the low m/z area and it is thus disadvantageous for structural identification to match with spectra library. If the EV is too low (for example, 10V), it is easy to obtain molecular ions. However, since there is few fragments and the response is low, it is also disadvantageous for identification process. Therefore, the EV is usually set at about 70V in practical application.

By taking EI-MS as example, the one-dimensional mass spectrum has the following problems. 1) It is hard to obtain a molecular ion peak at a default EV for molecules which are unstable and strongly polar and have a high molecular weight. 2) It is unable to know, from the one-dimensional mass spectrum, the change process of a certain ion peak in the mass spectrum. 3) In many cases, especially when substance have a relatively large molecular weight, the fragment ions have little difference in their molecular weight. These fragments and their numerous isotopic fragments will have extensive overlapping in the mass spectrum, making it difficult to assign the peaks to certain fragments. 4) It is unable to know, from the one-dimensional mass spectrum, the fragmentation kinetics of the substance under different parameters.

Similarly, it is also the case in the one-dimensional mass spectrum for $MS^n$. Generally, due to the interference of the overlapped peaks, multi-stage mass spectrometry is required for repeated fragmentation and analysis.

By the method of the present invention, a set of mass spectra (referred to as "two-dimensional mass spectra"

herein) are obtained in a certain mode and under different parameter settings. In this way, the fragmentation profile change for each ion can be known. For a certain fragment ion, since its parent ions and isotopic ions are absolutely kept in a certain proportion, a cluster of peaks for a same fragment ion are independent components in mass spectra under different conditions. For those alkane or olefin fragments with similar molecular weight, since they behave independently, it is able to distinguish them in the two-dimensional mass spectrum even if some of their isotopic peaks overlap. Once a certain independent ion (including its isotopic peaks) is determined, it is able to obtain the ionic formula (similar to molecular formula) of this independent ion quickly by the abundance and mass-to-charge ratio of its isotopic peaks. When the ionic formula for each independent ion of a certain substance is obtained, it is able to obtain the molecular formula of this substance quickly.

In addition, since each functional group in the molecules have different bond energy and spatial structures, they behave differently under different parameters. By utilizing the two-dimensional mass spectrum, it is able to distinguish the independent groups according to different fragmentation kinetics of the independent functional groups. In the mass spectrometric analysis, since the molecules of many isomers or homologues have the same groups, the difference in their one-dimensional mass spectra is not significant. Therefore, it is very difficult to distinguish isomers and homologues. However, since the isomers have different spatial structures and thus different kinetic processes, it is able to identify those isomers and homologues in conjunction with the small difference in their one-dimensional mass spectra.

In the detection and analysis method of the present invention, during the mass spectrometric analysis, the independent components (ions) and corresponding concentration change (kinetic processes) are found by: obtaining a two-dimensional mass spectrum by changing a certain parameter to add one or more perturbations, and then analyzing the two-dimensional mass spectrum by the entropy minimization algorithm. By the found independent components and their kinetic processes, the user can infer the chemical structural formula of those independent ions according to the mass spectrometric peaks (basic peaks and isotopic peaks) of those independent ions and further infer the structural formula of the whole substance to be detected. Further, the user can distinguish between isomers according to the kinetic processes of those independent ions, and determine the bond energy and possible spatial structure of bonds in the molecules.

Compared with the prior art, the detection and analysis method of the present invention can quickly and accurately perform qualitative analysis on the substances to be detected, no matter the substances are known or unknown, especially on substances that are difficult to distinguish with existing mass spectrometric techniques such as isomers and homologues. The method of the present invention can also separate them by the difference between the kinetic processes and thereby determine the nature of such substances. The method of the present invention has a very broad application prospect due to its simple operation and accurate results of analysis.

DETAILED DESCRIPTION OF THE INVENTION

The present invention will be described in detail by embodiments to make the features and advantages of the present invention clearer. However, it is to be noted that the embodiments are provided for understanding the concepts of the present invention, and the scope of the present invention is not limited to the embodiments listed herein.

The terms, as used in the present invention, have the meaning as usually understood by those skilled in the art, unless otherwise defined.

Figure 12:
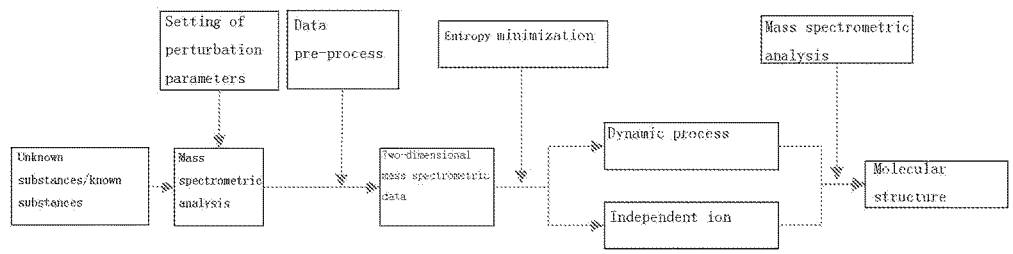
FIG. 12 is a simplified view showing a mass spectrometric detection and analysis process according to the present invention.

As shown in FIG. 12, the following steps are used to detect and analyze a substance to be detected (including unknown substances or known substances): setting one or more perturbation parameter conditions (i.e., perturbation conditions as described above) for a mass spectrometer, setting a corresponding set of different numeric values for the perturbation conditions, and performing mass spectrometric analysis on the substance to be detected under the different numeric values of the perturbation condition to obtain a set of mass spectrometric data;

then, calculating the obtained set of mass spectrometric data (two-dimensional mass spectrometric data) by an entropy minimization algorithm to obtain independent ions in the mass spectrum and the kinetic processes thereof; and then, performing mass spectrometric analysis on the obtained independent ions and the kinetic processes thereof to obtain the molecular structure of the substance to be detected.

Meanwhile, for some mass spectrometric data with a small response value, in order to realize better analysis by the entropy minimization algorithm, it is required to perform simple and conventional data pre-processing, comprising: performing linear transformation (for example, unitization, etc.) on a single piece of mass spectrometric data in the set of mass spectrometric data, or performing noise and background processing.

In the detection and analysis method of the present invention, during the mass spectrometric analysis, the independent components (ions) and corresponding concentration change (kinetic processes) are found by: obtaining a two-dimensional mass spectrum by changing a certain parameter to add one or more perturbations, and then analyzing the two-dimensional mass spectrum by the entropy minimization algorithm. By the found independent components and their kinetic processes, the user can infer the chemical structural formula of those independent ions according to the mass spectrometric peaks (basic peaks and isotopic peaks) of those independent ions and further infer the structural formula of the whole substance to be detected. Further, the user can distinguish between isomers according to the kinetic processes of those independent ions, and determine the bond energy and possible spatial structure of bonds in the molecules.

Embodiment 1

Instruments and chemicals: gas chromatography-mass spectrometer (GC-EI-MS), a mixture of dichloromethane and other components.

Figure 1:
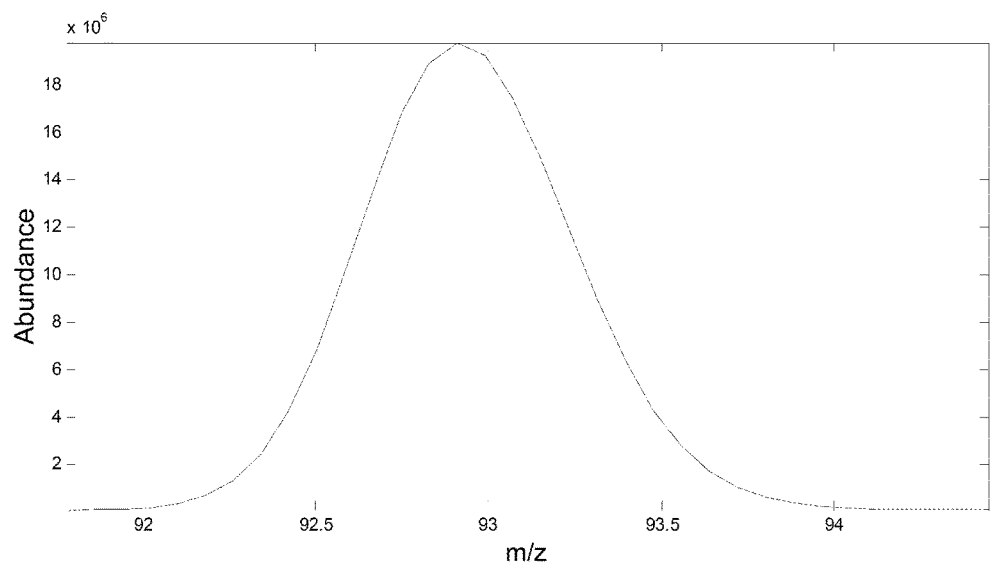
FIG. 1 shows a total ion chromatogram of dichloromethane at EV=30V, according to Embodiment 1 of the present invention.
Figure 2:
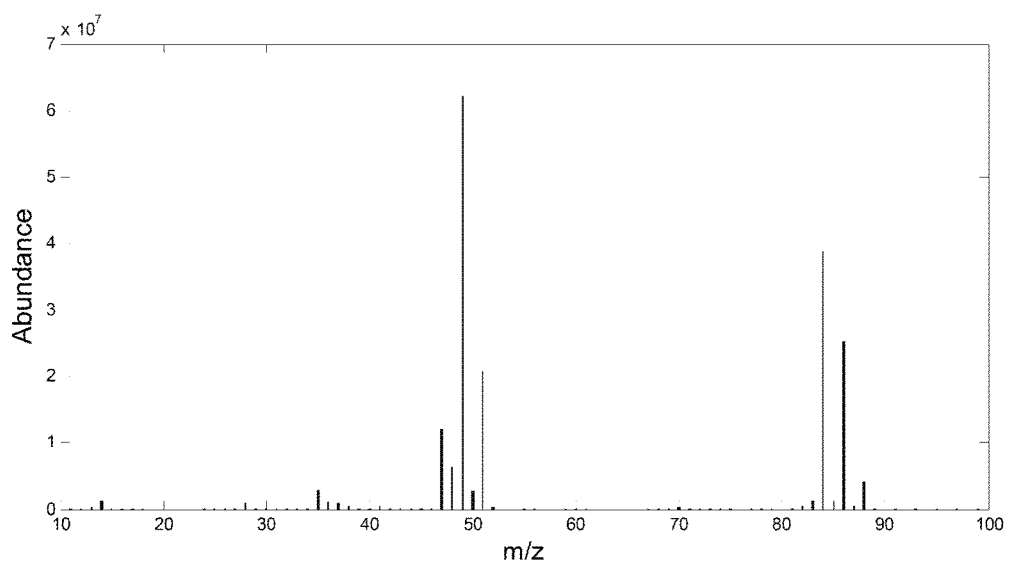
FIG. 2 shows mass spectrometric data after simply summing mass spectrometric data obtained in FIG. 1 at different retention time.

Experimental conditions: under same experimental conditions and by changing the EV only (EV ranges from 10V to 70V, at an interval of 5V, total thirteen experiments), the mixture was analyzed by the GC-EI-MS in equal amount to obtain total thirteen pieces of experimental data. As shown in FIG. 1 and FIG. 2, the pieces of experimental data at EV=30V are shown. That is, the "one-dimensional mass spectrum" which is usually detected.

Data processing: in each piece of experimental data, according to the retention time of dichloromethane, the pieces of mass spectrometric data obtained by experiments and at different retention time were simply summed within the same retention time range to obtain one piece of mass spectrometric data. From the thirteen pieces of GC-MS data, total thirteen pieces of mass spectrometric data were eventually obtained. The thirteen pieces of data were aggregated and analyzed by the entropy minimization algorithm.

Figure 3:
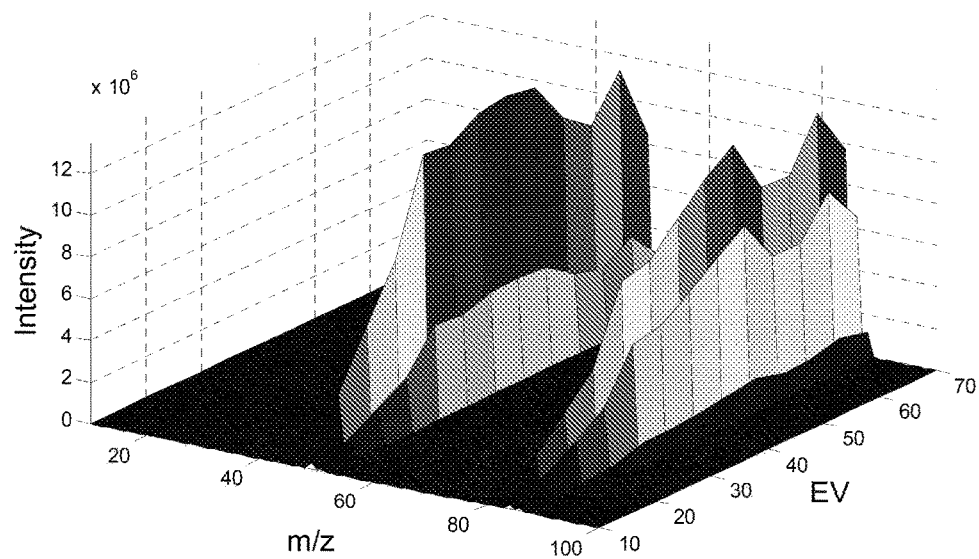
FIG. 3 is a three-dimensional view of thirteen mass spectra obtained at 13 different EVs, according to Embodiment 1 of the present invention.

As known from FIG. 3, in the GC-MS, the abundance of the fragment ions is very low when the EV is low, while high when the EV is high. The inventor has found that the total abundance is 9.872E5 at EV=10V, and 5.265E7 at EV=50V, which is 53 times of the abundance at EV=10V. Based on such data, it is unable to analyze the independent ions well by the entropy minimization algorithm. This is because, when the EV is low, since the abundance of ions is very low, the change in ions can be ignored when compared with the change in ions when the EV is high. That is, the change in ions is overwhelmed. In other words, the change in ions when the EV is low can be ignored when compared with the change in ions when the EV is high, regardless of how ions change when the EV is low.

Figure 4:
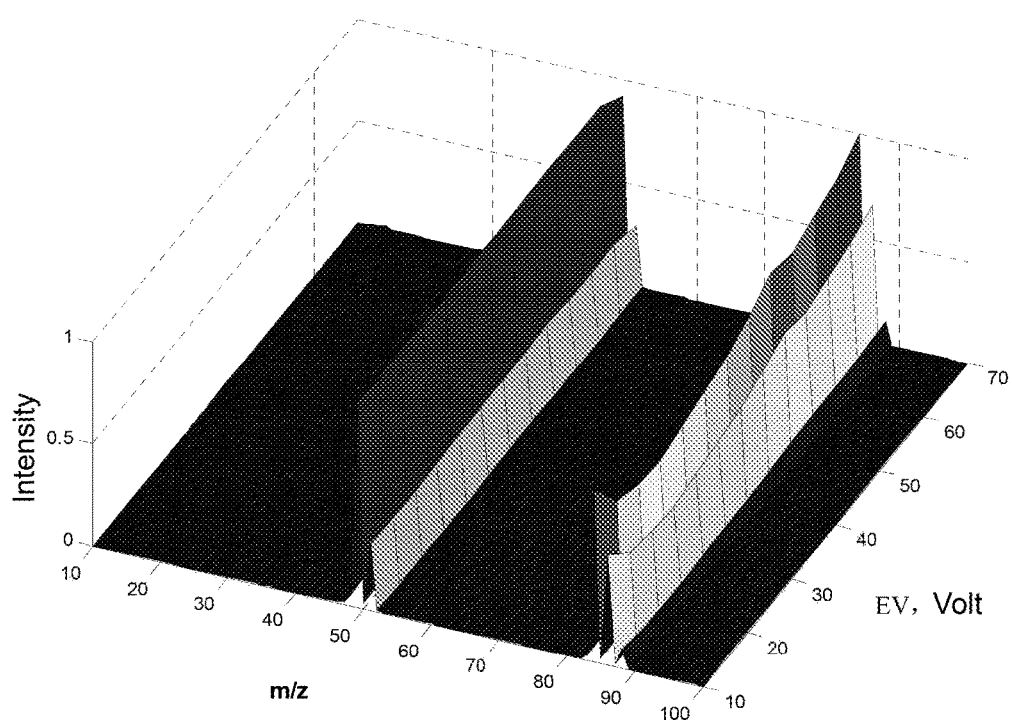
FIG. 4 is a three-dimensional view of thirteen mass spectra after unitizing the highest peaks of FIG. 3.

In order to solve such a problem, each mass spectrum at different EVs is unitized by using the value of its highest abundance. In other words, in the unitized mass spectrum, the highest peaks of ions have a numeric value of 1 or a certain fixed numeric value, and other ion peaks change correspondingly, as shown in FIG. 4.

Figure 5A:
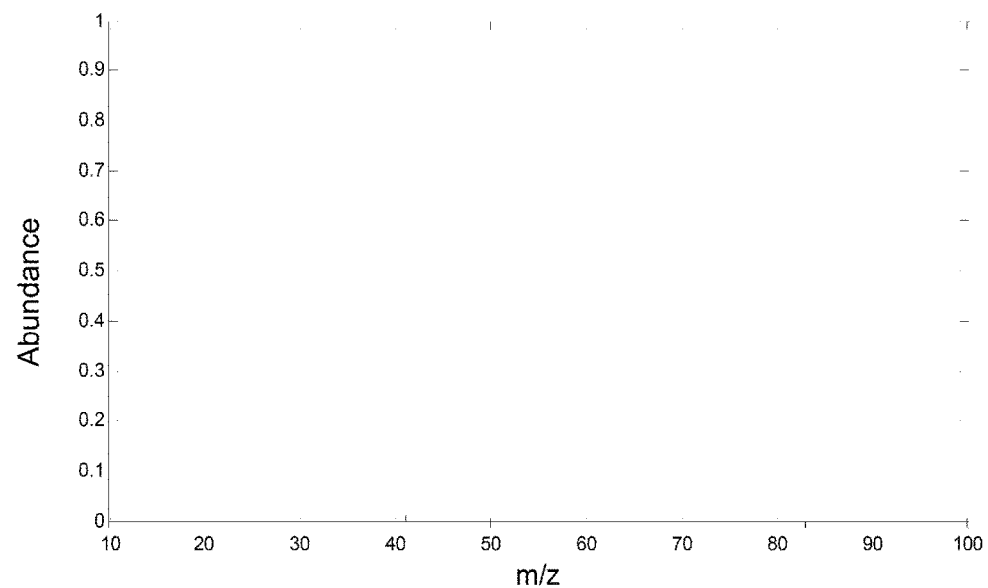
FIG. 5 shows basic peaks of $CH_2Cl_2^+$ (FIG. 5A) and ion mass spectrometric peaks of $CH_2Cl^+$ (FIG. 5B), according to Embodiment 1 of the present invention.
Figure 5B:
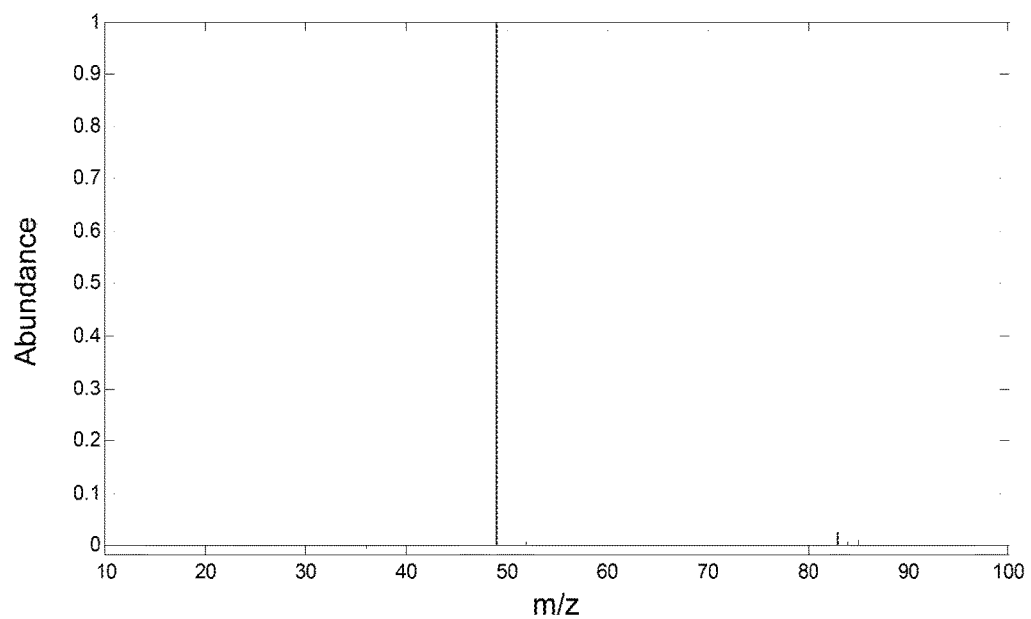

By the entropy minimization algorithm [for example, W. Chew, E. Widjaja, M. Garland, Organometallics, 21 (2002) 1982-1990, N. J. Zhang, M. Garland, Y. Z. Zeng, P. Wu, J Am Soc Mass Spectrom, 14 (2003) 1295-1305, and N. J. Zhang, W. Chew, M. Garland, Applied Spectroscopy, 61 (2007) 1366-1372], the pure spectra of the independent components can be found; two independent group ions can be found by calculation; then, they are determined as $CH_2Cl_2^+$ and $CH_2Cl^+$, by using the intensity ratio calculation method of isotopic peaks and according to the distribution of their isotopic peaks and the m/z value, as shown in FIG. 5A and FIG. 5B.

With regard to a cluster of mass spectrometric peaks of independent ions $CH_2Cl_2^+$ or $CH_2Cl^+$, it is unable to determine whether the cluster of peaks are formed by a kind of ions or by different kinds of ions in the one-dimensional mass spectrum since there are many peaks, if the compound to be analyzed is unknown. The user can consider that a cluster of peaks are formed by two different ions, for example, fragment ion peaks of the saturated alkanes containing the same number of carbon atoms and fragment ion peaks of the olefins containing one double-bond. In the one-dimensional mass spectrum, since it is unable to determine independent ions, it is unable to determine what the ions are by the possible molecular weight of the ions (for example, for a mass spectrometric peak having a basic peak at 28, it may be a peak of $CO^+$ or $N_2^+$).

However, by the analysis by the entropy minimization algorithm, it is able to determine that a cluster of peaks of independent ions $CH_2Cl_2^+$ or $CH_2Cl^+$ are mass spectrometric peaks of one ion. According to the distribution of isotopic peaks thereof and the m/z value, an experienced user can immediately know that the ion is an ion containing Cl element and further judge whether the ion is $CH_2Cl_2^+$ or $CH_2Cl^+$. Even an inexperienced user can judge whether the ion is $CH_2Cl_2^+$ or $CH_2Cl^+$ by comparing the m/z value and the distribution of peaks by third-party software (for example, NIST14). Based on the structural information of those independent ions and the obtained molecular ion peaks, the user can know that the compound is $CH_2Cl_2$.

Figure 6A:
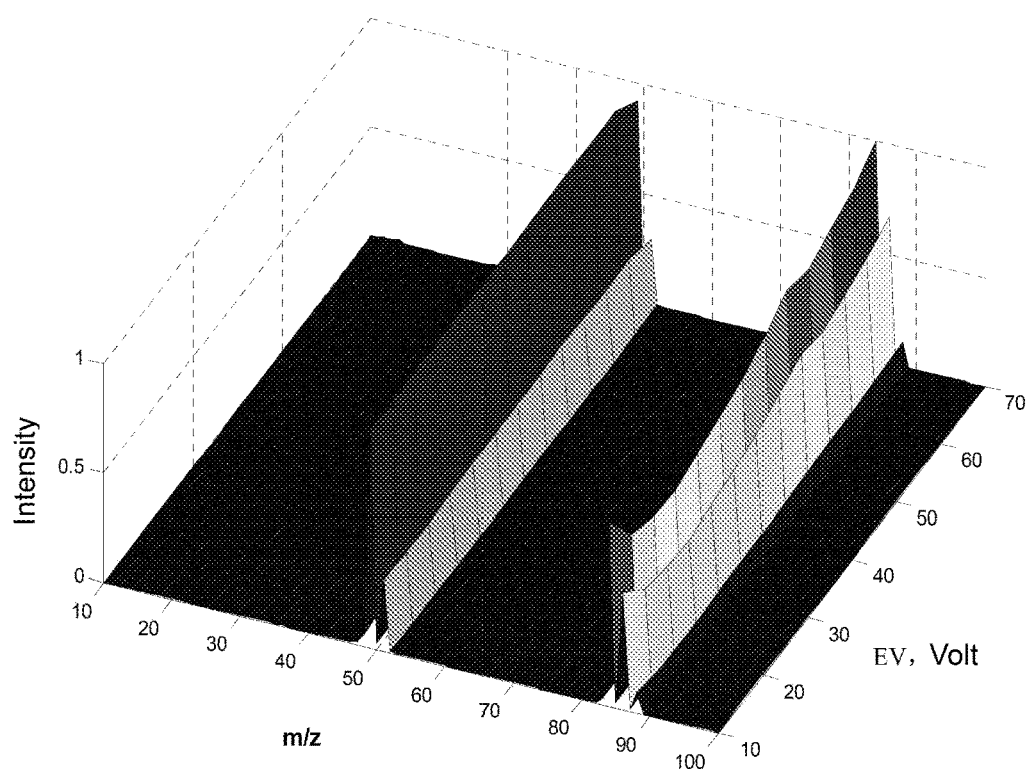
FIG. 6 shows a two-dimensional mass spectrum (FIG. 6A) and fragmentation kinetics profile of independent ions (FIG. 6B), after unitizing the highest peaks, according to Embodiment 1 of the present invention.
Figure 6B:
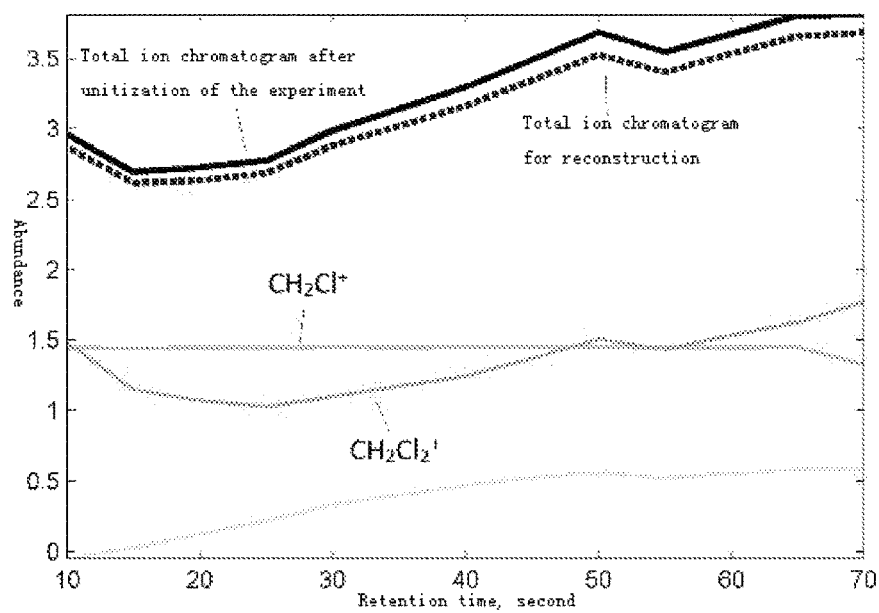

However, the physical significance of the kinetic results is not obvious if each one-dimensional spectrum is simply unitized by the highest peaks. FIG. 6A and FIG. 6B show kinetic processes of each independent fragment at a varying EV. Since the highest peaks are unitized to 1, the reconstructed "concentration" of $CH_2Cl^+$ is substantially a straight line. Although some problems are illustrated, the actual physical significance is not so clear.

Figure 7A:
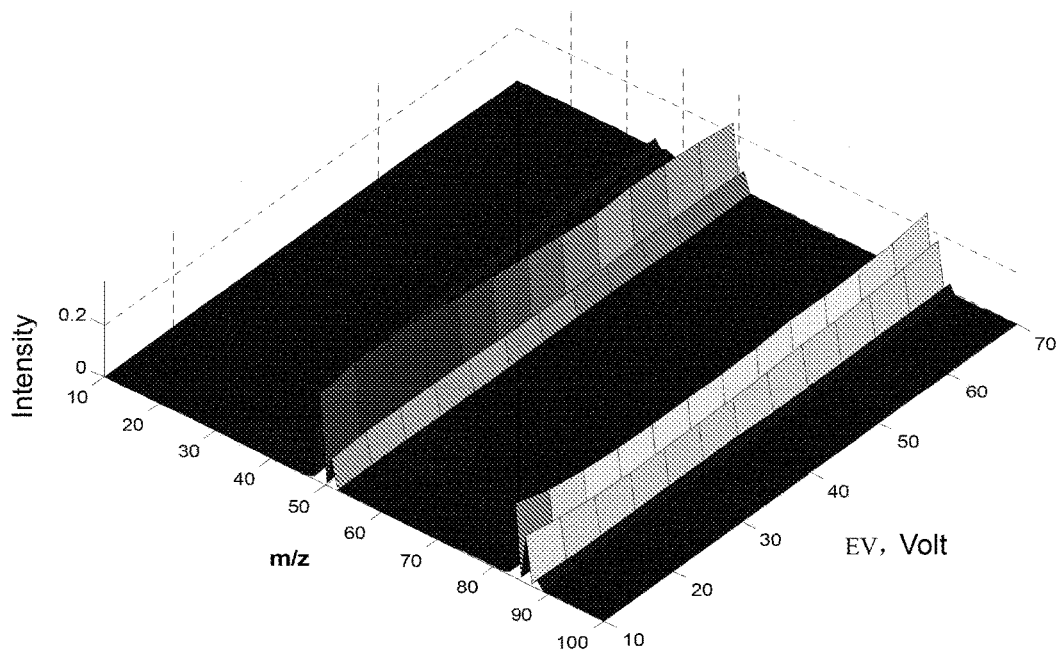
FIG. 7 shows a two-dimensional mass spectrum (FIG. 7A) and kinetic processes of independent ions (FIG. 7B), after unitizing the highest peaks in the whole spectrum in another way, according to Embodiment 1 of the present invention.
Figure 7B:
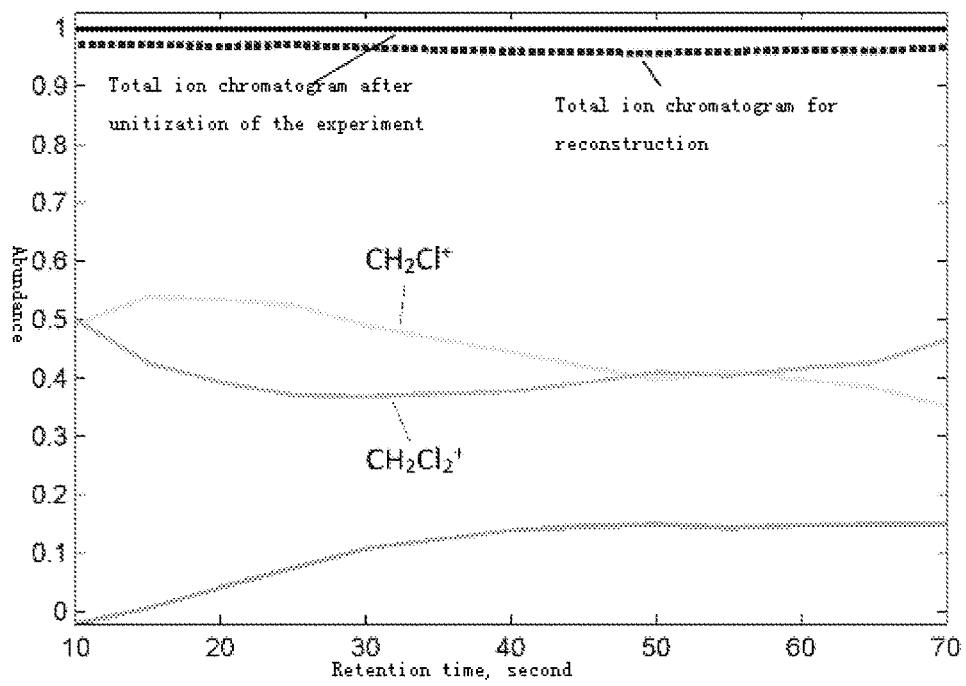

As another unitization method, in the one-dimensional mass spectrum at each different EV, the values of all data channels are summed, the summed value is changed to 1 or a certain numeric value, and then the value of each data channel is unitized by using this numeric value. In such a unitization method, the concentration of any one independent ion can be considered as the percentage of this independent ion in all the independent ions. By such a unitization method, their two-dimensional mass spectrometric data are shown in FIG. 7A and FIG. 7B. By using the entropy minimization algorithm, the kinetic processes of the independent ions are obtained, as shown in FIG. 7A and FIG. 7B.

As shown, in the mass spectrum, the concentration in percentage of the molecular ion ($CH_2Cl_2^+$) of dichloromethane starts to decrease as the EV increases, and starts to increase at about EV=30. In contrast, the concentration of the daughter ion $CH_2Cl^+$ increases and then decreases. Such a kinetic process may be caused for the following reason: since when the EV is low, molecules cannot be broken even if they are charged due to the low collision energy, but the molecules can be broken as the energy increases; in this case, the concentration of the ion $CH_2Cl^+$ starts to increase, and the concentration of the ion $CH_2Cl_2^+$ starts to decrease. As the EV continuously increases, the ion $CH_2Cl^+$ is broken by electrons with higher energy. Therefore, the concentration of the ion $CH_2Cl^+$ decreases. Thus, it is able to know the fragmentation process of molecules in the mass spectrometry based on the reaction kinetics of independent ions at different EVs. For isomers, the fragmentation kinetics of the isomers are different since they have different spatial structures, different bond positions and different bond energy. It is thus able to distinguish them.

In addition, it is very difficult for many substances having a high molecular weight to obtain complete molecular ion peaks at common EV=70V because they are easily broken in the mass spectrometry. In contrast, it is easy for such substances to obtain molecular ion peaks at a low EV. In additional, in the one-dimensional mass spectrum, peaks having a greater mass-to-charge ratio than molecular ion peaks may occur sometimes due to the interference from the background. Therefore, it is hard to make a determination. By changing the EV and in conjunction with the EM, it is able to know the independent ions and kinetic processes thereof, and also able to easily obtain the separated ion peaks and to remove the interference of the background to quickly determine the molecular ion peaks.

Similarly, during the liquid chromatography-mass spectrometry, the mass spectrum of many fragment ions may occur after certain unknown substances in the one-dimensional mass spectrum are broken (for example, by tandem mass spectrometry or ion trap mass spectrometry). A two-dimensional mass spectrum may be formed by changing the accelerating voltage and the like. Mathematically, the two-dimensional mass spectrum from the liquid chromatography-mass spectrometry and the two-dimensional mass spectrum from GC-EI-MS are substantially the same for the EM method. Thus the kinetic studies can still be used to give information on all the independent ions and their kinetics which can be pieced together to obtain the information of the parent ion.

Embodiment 2

In one EI-MS instrument, the pure dichloromethane was slowly injected directly into a mass spectrometer by a micro-injection pump, and at the same time, the EV was changed. The other experimental conditions were kept consistent with those in Embodiment 1. Sampling analysis was performed for many times. Then, data at different EVs was collected and then calculated by EM to obtain the independent ions and reaction kinetics thereof.

In this experiment, the results are consistent with those in Embodiment 1. Independent ions $CH_2Cl_2^+$ and $CH_2Cl^+$, and kinetic processes thereof, are also found.

Embodiment 3

In one liquid chromatography tandem mass spectrometer with ESI ionization, the sulfadoxine solution was injected directly into the mass spectrometer by an injection pump, with a feeding rate of 100 μL/min. The solvent for the sulfadoxine solution is 50% methanol-water solution, and the concentration of the sulfadoxine is 1.0 μg/mL. The mass spectrometric detection mode is ESI+.

Figure 8:
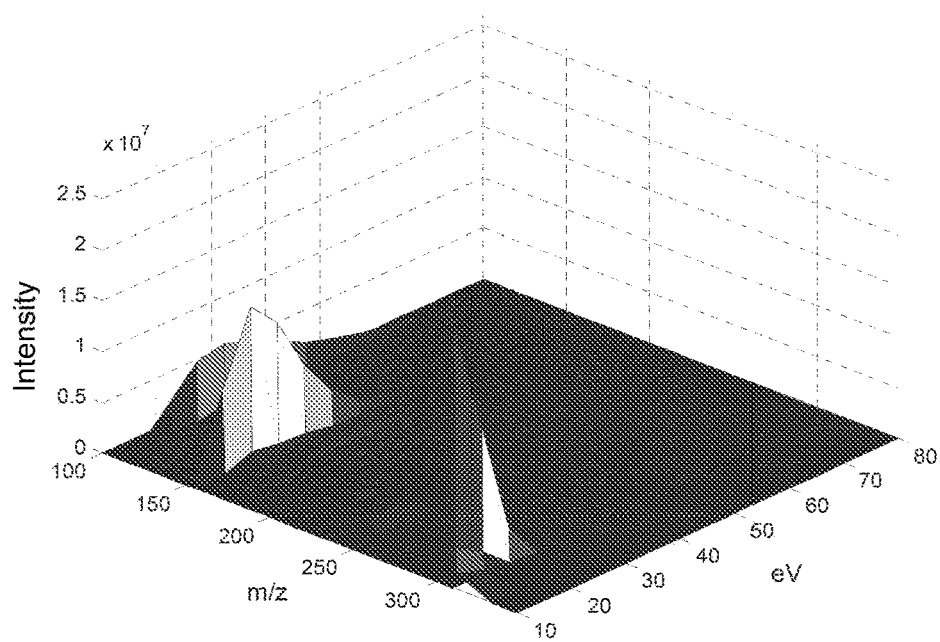
FIG. 8 shows an $MS^2$ spectrum obtained at different CID voltages, according to Embodiment 3 of the present invention.

The parent ions of the sulfadoxine were dissociated under different Collision-Induced Dissociation (CID) collision energy (10 eV to 80 eV, with an interval of 5 eV), the $MS^2$ mass spectra of its daughter ions were scanned and recorded, and finally fifteen $MS^2$ mass spectra are collected, as shown in FIG. 8.

In the $MS^2$ mass spectra in this embodiment, since the sulfadoxine solution was injected by an injection pump at a uniform feeding rate, the concentration of the parent ions remains unchanged. In the subsequent stage, since the parent ions are dissociated and the uncharged particles and negatively charged particles cannot be recorded, the overall abundance decreases as the dissociation energy increases. This process is different from the two-dimensional mass spectrum obtained by changing the EV in the gas chromatography-mass spectrometry, and the resulting data is not to be unitized.

Figure 9:
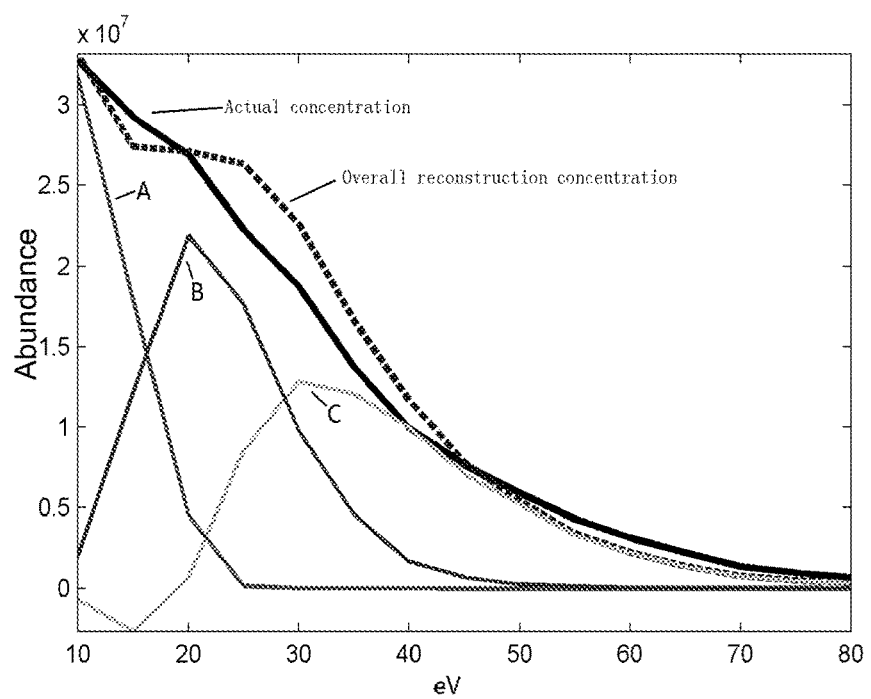
FIG. 9 shows reconstructed concentrations, the total reconstructed concentration and the actual concentration corresponding to independent ions A, B and C obtained by reconstruction, according to Embodiment 3 of the present invention.
Figure 10A:
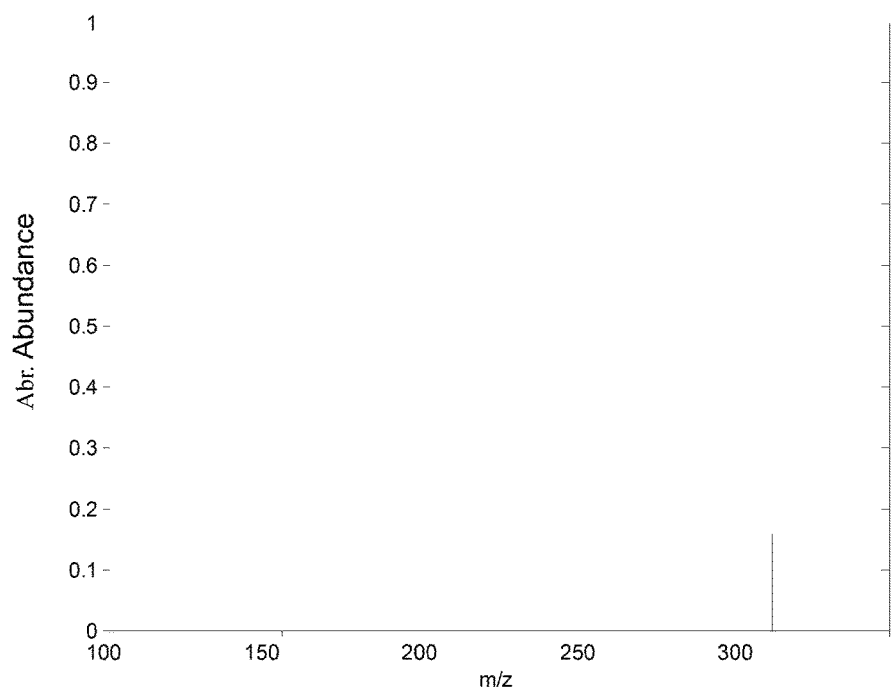
FIGS. 10A-C show mass spectra of independent ions A, B and C obtained by reconstruction, respectively, according to Embodiment 3 of the present invention.
Figure 10B:
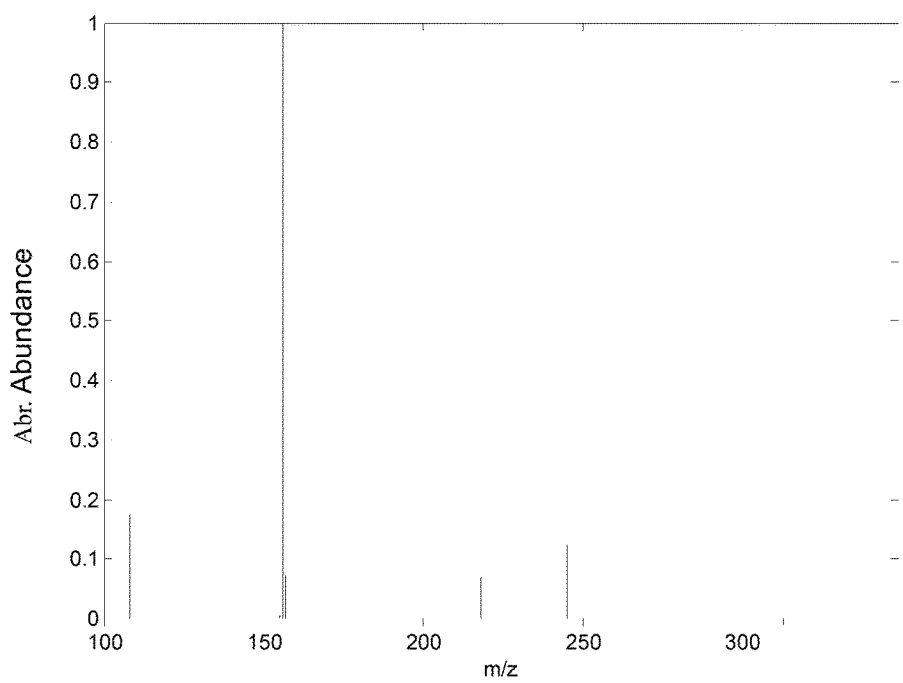
Figure 10C:
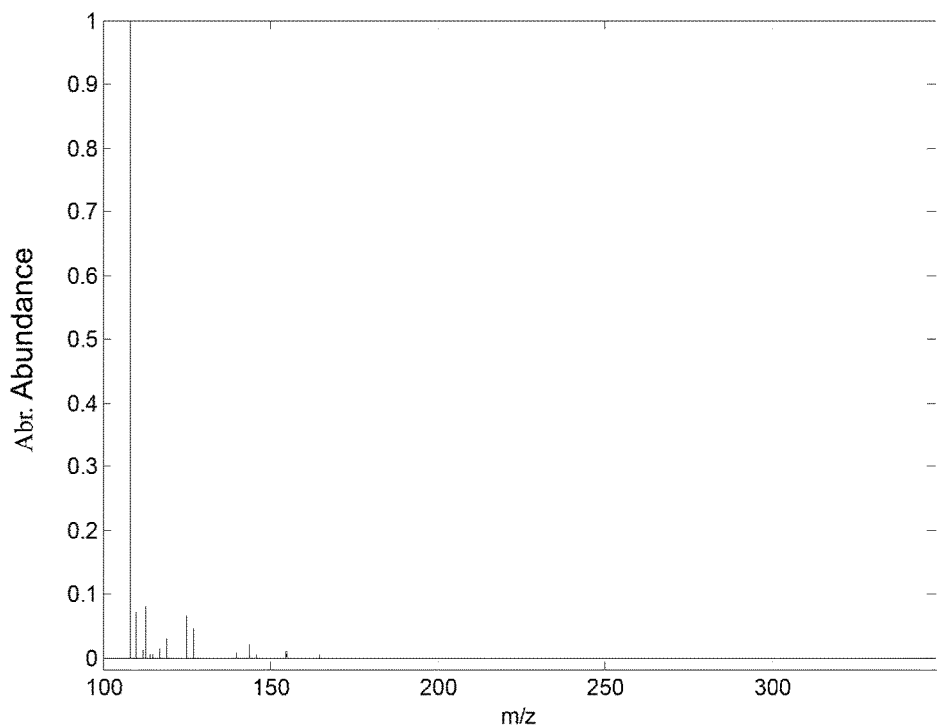

The EM algorithm was performed on the non-unitized two-dimensional $MS^2$ data to obtain the independent ions A, B and C and kinetic profile thereof, as shown in FIG. 9. In this drawing, the total reconstruction concentration is the sum of all reconstruction concentrations of A, B and C. The mass spectra of the independent ions obtained by reconstruction, corresponding to the reconstruction concentrations, are shown in FIG. 10A, FIG. 10B and FIG. 10C.

As shown in FIG. 9, this dissociation process has three obvious steps. The kinetic processes are quite clear: A generates B and then B generates C.

(1) Dissociation of Parent Ions A

The parent ion was dissociated into four main second-level ions B as the dissociation voltage increases, and when the dissociation voltage reached 25 eV, the parent ion was almost decomposed completely.

(2) Generation and Dissociation of Second-Level Ions B

With the dissociation of the parent ion A, the parent ion A was dissociated into four second-level ions which were all separated from the parent ion and kept in a consistent proportion. Therefore, the four second-level ions were reconstructed as an independent cluster. As the dissociation voltage continuously increases, and also because of the decrease of the parent ion A and the dissociation of the second-level ions B, the number of the second-level ions B started to reach a maximum number at about 20 eV and then started to decrease. The second-level ions B were dissociated completely at 45 eV.

(3) Generation and Dissociation of Third-Level Ions C

As shown, the generation of third-level ions C was resulted from the dissociation of the second-level ions B. With the dissociation of the second-level ions B, the number of the third-level ions C started to increase later (20 eV). As the dissociation of the second-level ions B continues, the number of the third-level ions C started to increase. Meanwhile, since ions among the second-level ions B were dissociated simultaneously, a lot of different fragment ions were generated, and therefore, there are many kinds of third-level ions.

Figure 11:
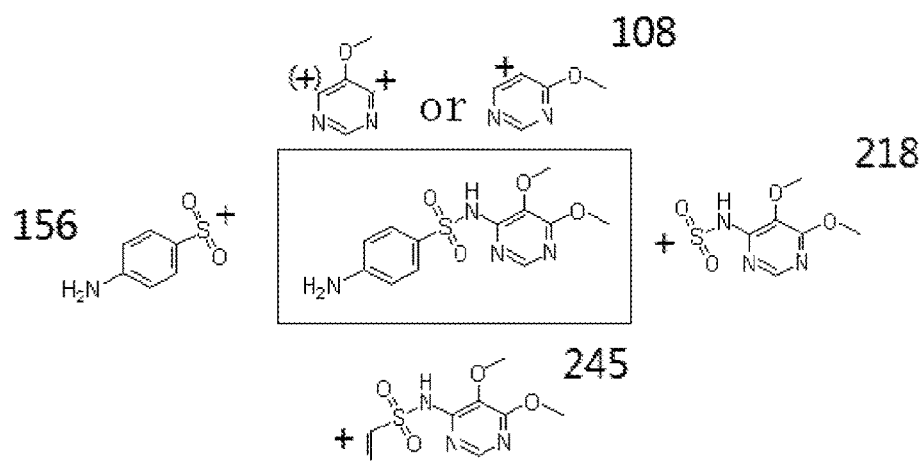
FIG. 11 shows a molecular formula of sulfadoxine and chemical formula of ions fragmented simultaneously during the $MS^2$ analysis.

This result clearly indicates that the parent ion A is dissociated into four daughter ions at the same time. This cannot be found in the one-dimensional $MS^2$ mass spectrum. The mass-to-charge ration of those four daughter ions is, respectively, 108, 156, 218 and 245. The molecular formula of the sulfadoxine and the chemical formula of the ions are shown in FIG. 11.

According to the proportion of peak height of components in the second-level ions B, the proportion in percentage of ions in the second-level ions B is:

at m/z=108, 12.7%; at m/z=156, 73.1%; at m/z=218, 5.1%; and at m/z=245, 9.1%, respectively.

Those proportions in percentage are proportions of ions in the second-level ions B generated by the parent ion A. According to those proportions and the kinetic results and by using the conventional techniques, the user can perform further analysis to obtain more information, so as to obtain the structure of the substance to be detected and the like.

For the third-level ions C, the highest ion peak is at m/z=108, the same as the lowest peak for the second-level ions C. This result indicates that this algorithm can deal with overlapped peaks. This result also indicates that the structural formula of the second-level ions at m/z=218 and m/z=245 are correct, because they contain fragments at m/z=108.

The implementations described herein are only exemplary, but used for limiting the protection scope of the present invention. Various other replacements, changes and improvements may be made by those skilled in the art without departing from the scope of the present invention. For example, it is possible for those skilled in the art to analyze the kinetics of the independent ions according to multi-dimensional mass spectra and other algorithms by referencing or exploiting the concepts of the present invention to realize the same effects. Therefore, the present invention is not limited to the implementations described above, and defined by the appended claims only.

The invention claimed is:

1. A mass spectrometric detection and analysis method, comprising the steps of:
   1) selecting, one or more parameters of a mass spectrometer as perturbation condition during detection, setting a set of different numeric values for the perturbation condition, detecting by the mass spectrometer a substance under the different numeric values of the perturbation condition to obtain a set of mass spectrometric data and using m/z, peak intensity, and the perturbation condition as three axes to form a two-dimensional mass spectrum of the substance;
   2) analyzing the two-dimensional mass spectrum by an entropy minimization algorithm to obtain independent ions formed by fragmentation of the substance in the mass spectrometric data and fragmentation processes thereof; and
   3) performing mass spectrometric analysis on the basis of the independent ions and the fragmentation processes thereof obtained in the step 2) to obtain structural information of the substance,
   wherein the perturbation condition of step 1) comprises one or more of electron ionization voltage, degree of vacuum, ion accelerating voltage and collision energy.

2. The method according to claim 1, characterized in that the perturbation condition further comprises one or more of magnetic field strength, radiation strength, size and type of collided molecules, and wavelength or strength of an excitation light source.

3. The method according to claim 1, characterized in that the step 1) further comprises: pre-processing the mass spectrometric data.

4. The method according to claim 3, characterized in that the data pre-processing comprises: performing linear transformation on a single piece of mass spectrometric data.

5. The method according to claim 3, characterized in that the data pre-processing comprises: de-noising and background processing.

6. The method according to claim 1, characterized in that the fragmentation processes of each independent ion, as described in the step 2) and the step 3), correspond to the change in concentration of each independent ion.

7. The method according to claim 1, characterized in that the step 3) further comprises: obtaining, by analysis, the structure of the independent ions before obtaining the structure of the substance.

8. The method according to claim 1, characterized in that the step 3) further comprises: inferring a chemical structural formula of each independent ion according to the mass spectrometric peaks of each independent ion, and further inferring a structural formula of the substance, the mass spectrometric peaks comprising at least one of basic peaks and isotopic peaks.

9. The method according to claim 1, characterized in that the step 3) further comprises: distinguishing between isomers according to the fragmentation process of each independent ion, and further determining the bond energy and spatial structure of bonds in the molecules of the substance.

10. The method according to claim 1, characterized in that the mass spectrometer comprises a gas chromatography-mass spectrometer or a liquid chromatography-mass spectrometer.

11. The method according to claim 1, characterized in that the ionization mode for the mass spectrometer comprises chemical ionization, electron ionization, electrospray ionization or atmospheric pressure chemical ionization.

12. The method according to claim 1, characterized in that the substance comprises mixture components.

13. A mass spectrometric detection and analysis method, comprising the steps of:
   1) selecting, collision induced dissociation (CID) collision energy as perturbation condition during detection, setting a set of different numeric values for the CID collision energy, detecting by the mass spectrometer a substance under the different numeric values of the CID collision energy to obtain a set of mass spectrometric data and using m/z, peak intensity, and the CID collision energy to form a two-dimensional mass spectrum of the substance;
   2) analyzing the two-dimensional mass spectrum by an entropy minimization algorithm to obtain independent ions formed by fragmentation of the substance in the mass spectrometric data and fragmentation processes thereof; wherein the fragmentation processes of each independent ion corresponds to the change in concentration of each independent ion; and
   3) performing mass spectrometric analysis on the basis of the independent ions and the fragmentation processes thereof obtained in the step 2) by inferring a chemical structural formula of each independent ion according to the mass spectrometric peaks of each independent ion and further inferring a structural formula of the substance, wherein the mass spectrometric peaks comprising at least one of basic peaks and isotopic peaks.

14. The method according to claim 13, characterized in that the step 1) further comprises: pre-processing the mass spectrometric data.

15. The method according to claim 14, characterized in that the data pre-processing comprises: performing linear transformation on a single piece of mass spectrometric data.

16. The method according to claim 14, characterized in that the data pre-processing comprises: de-noising and background processing.

17. The method according to claim 13, characterized in that the step 3) further comprises: distinguishing between isomers according to the fragmentation process of each independent ion, and further determining the bond energy and spatial structure of bonds in the molecules of the substance.

18. The method according to claim 13, characterized in that the mass spectrometer comprises a gas chromatography-mass spectrometer or a liquid chromatography-mass spectrometer.

19. The method according to claim 13, characterized in that the ionization mode for the mass spectrometer comprises chemical ionization, electron ionization, electrospray ionization or atmospheric pressure chemical ionization.

20. The method according to claim 13, characterized in that the setting a set of different numeric values for the CID collision energy, detecting by the mass spectrometer a substance under the different numeric values of the CID collision energy to obtain a set of mass spectrometric data step comprises setting a set of collision energy between 10 to 80 V with a step of 5 V and to obtain a set of 15 mass spectrometric data.

* * * * *